United States Patent
Al-Ali et al.

(10) Patent No.: US 9,867,578 B2
(45) Date of Patent: Jan. 16, 2018

(54) PHYSIOLOGICAL ACOUSTIC MONITORING SYSTEM

(71) Applicant: Masimo Corporation, Irvine, CA (US)

(72) Inventors: Ammar Al-Ali, San Juan Capistrano, CA (US); Sung Uk Lee, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 15/204,773

(22) Filed: Jul. 7, 2016

(65) Prior Publication Data

US 2017/0007190 A1     Jan. 12, 2017

Related U.S. Application Data

(60) Continuation of application No. 14/473,831, filed on Aug. 29, 2014, now Pat. No. 9,386,961, which is a division of application No. 12/905,036, filed on Oct. 14, 2010, now Pat. No. 8,821,415.

(60) Provisional application No. 61/391,098, filed on Oct. 8, 2010, provisional application No. 61/252,099, filed on Oct. 15, 2009.

(51) Int. Cl.
| | |
|---|---|
| *A61B 5/00* | (2006.01) |
| *A61B 7/00* | (2006.01) |
| *A61B 7/04* | (2006.01) |
| *A61B 5/0205* | (2006.01) |

(Continued)

(52) U.S. Cl.
CPC .......... *A61B 5/7415* (2013.01); *A61B 5/0002* (2013.01); *A61B 5/4803* (2013.01); *A61B 5/6833* (2013.01); *A61B 5/7282* (2013.01); *A61B 7/003* (2013.01); *A61B 7/008* (2013.01); *A61B 7/04* (2013.01); *A61B 5/024* (2013.01); *A61B 5/0205* (2013.01); *A61B 5/0816* (2013.01); *A61B 5/4818* (2013.01); *A61B 5/7232* (2013.01); *A61B 2562/0204* (2013.01)

(58) Field of Classification Search
CPC ..... A61B 7/003; A61B 5/0205; A61B 5/4818; A61B 5/024; A61B 5/0816; A61B 5/7232
See application file for complete search history.

(56) References Cited

U.S. PATENT DOCUMENTS

| | | |
|---|---|---|
| 3,399,467 A | 9/1968 | Ravin |
| 3,682,161 A | 8/1972 | Alibert |

(Continued)

FOREIGN PATENT DOCUMENTS

| | | |
|---|---|---|
| CA | 2490438 | 1/2004 |
| CA | 2262236 | 4/2008 |

(Continued)

OTHER PUBLICATIONS

US 8,740,816, 06/2014, Telfort et al. (withdrawn)

(Continued)

*Primary Examiner* — Max Hindenburg
(74) *Attorney, Agent, or Firm* — Knobbe, Martens, Olson & Bear, LLP

(57) ABSTRACT

An acoustic monitoring system has an acoustic front-end, a first signal path from the acoustic front-end directly to an audio transducer and a second signal path from the acoustic front-end to an acoustic data processor via an analog-to-digital converter. The acoustic front-end receives an acoustic sensor signal responsive to body sounds in a person. The audio transducer provides continuous audio of the body sounds. The acoustic data processor provides audio of the body sounds upon user demand.

16 Claims, 9 Drawing Sheets

(51) Int. Cl.
  *A61B 5/024* (2006.01)
  *A61B 5/08* (2006.01)

(56) References Cited

U.S. PATENT DOCUMENTS

| | | |
|---|---|---|
| 3,951,230 A | 4/1976 | Littmann |
| 4,127,749 A | 11/1978 | Atoji et al. |
| 4,254,302 A | 3/1981 | Walshe |
| 4,326,143 A | 4/1982 | Guth et al. |
| 4,413,202 A | 11/1983 | Krempl et al. |
| 4,537,200 A | 8/1985 | Widrow |
| 4,576,179 A | 3/1986 | Manus et al. |
| 4,578,613 A | 3/1986 | Dorogusker et al. |
| 4,634,917 A | 1/1987 | Dvorsky et al. |
| 4,653,498 A | 3/1987 | New, Jr. et al. |
| 4,672,976 A | 6/1987 | Kroll |
| 4,805,633 A | 2/1989 | Kotani et al. |
| 4,827,943 A | 5/1989 | Bornn et al. |
| 4,871,046 A | 10/1989 | Turner |
| 4,884,809 A | 12/1989 | Rowan |
| 4,924,876 A | 5/1990 | Cameron |
| 4,947,859 A | 8/1990 | Brewer et al. |
| 4,960,118 A | 10/1990 | Pennock |
| 4,960,128 A | 10/1990 | Gordon et al. |
| 4,964,408 A | 10/1990 | Hink et al. |
| 4,982,738 A | 1/1991 | Griebel |
| 5,003,605 A | 3/1991 | Phillipps et al. |
| 5,033,032 A | 7/1991 | Houghtaling |
| 5,036,857 A | 8/1991 | Semmlow et al. |
| 5,041,187 A | 8/1991 | Hink et al. |
| 5,069,213 A | 12/1991 | Polczynski |
| 5,078,151 A | 1/1992 | Laballery |
| 5,140,992 A | 8/1992 | Zuckerwar et al. |
| 5,143,078 A | 9/1992 | Mather et al. |
| 5,163,438 A | 11/1992 | Gordon et al. |
| 5,269,314 A | 12/1993 | Kendall et al. |
| 5,278,627 A | 1/1994 | Aoyagi et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| 5,406,952 A | 4/1995 | Barnes et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,448,996 A | 9/1995 | Bellin et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,539,831 A | 7/1996 | Harley |
| 5,561,275 A | 10/1996 | Savage et al. |
| 5,562,002 A | 10/1996 | Lalin |
| 5,564,108 A | 10/1996 | Hunsaker et al. |
| 5,578,799 A | 11/1996 | Callahan et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,730,140 A | 3/1998 | Fitch |
| D393,830 S | 4/1998 | Tobler et al. |
| 5,738,106 A | 4/1998 | Yamamori et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,812,678 A | 9/1998 | Scalise et al. |
| 5,823,950 A | 10/1998 | Diab et al. |
| 5,825,895 A | 10/1998 | Grasfield et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,912,656 A | 6/1999 | Tham et al. |
| 5,919,134 A | 7/1999 | Diab |
| 5,934,925 A | 8/1999 | Tobler et al. |
| 5,940,182 A | 8/1999 | Lepper, Jr. et al. |
| 5,977,538 A | 11/1999 | Unger et al. |
| 5,989,193 A | 11/1999 | Sullivan |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,048,323 A | 4/2000 | Hon |
| 6,067,462 A | 5/2000 | Diab et al. |
| 6,081,735 A | 6/2000 | Diab et al. |
| 6,083,156 A | 7/2000 | Lisiecki |
| 6,088,607 A | 7/2000 | Diab et al. |
| 6,106,481 A | 8/2000 | Cohen |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,168,568 B1 | 1/2001 | Gavriely |
| 6,184,521 B1 | 2/2001 | Coffin, IV et al. |
| 6,206,830 B1 | 3/2001 | Diab et al. |
| 6,210,344 B1 | 4/2001 | Perin et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,248,083 B1 | 6/2001 | Smith et al. |
| 6,253,097 B1 | 6/2001 | Aronow et al. |
| 6,256,523 B1 | 7/2001 | Diab et al. |
| 6,261,237 B1 | 7/2001 | Swanson et al. |
| 6,263,222 B1 | 7/2001 | Diab et al. |
| 6,271,760 B1 | 8/2001 | Watanabe et al. |
| 6,275,594 B1 | 8/2001 | Senoo et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,295,365 B1 | 9/2001 | Ota |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,415,033 B1 | 7/2002 | Halleck et al. |
| 6,423,013 B1 | 7/2002 | Bakker et al. |
| 6,430,437 B1 | 8/2002 | Marro |
| 6,430,525 B1 | 8/2002 | Weber et al. |
| 6,438,238 B1 | 8/2002 | Callahan |

(56) References Cited

U.S. PATENT DOCUMENTS

| | | |
|---|---|---|
| 6,463,311 B1 | 10/2002 | Diab |
| 6,470,199 B1 | 10/2002 | Kopotic et al. |
| 6,486,588 B2 | 11/2002 | Doron et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,517,497 B2 | 2/2003 | Rymut et al. |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,702,755 B1 | 3/2004 | Stasz et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,074 B1 | 4/2004 | Kästle |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,816,744 B2 | 11/2004 | Garfield et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,937,736 B2 | 8/2005 | Toda |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,954,971 B1 | 10/2005 | Bryant et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,020,508 B2 | 3/2006 | Stivoric et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,035,684 B2 | 4/2006 | Lee |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,096,060 B2 | 8/2006 | Arand et al. |
| 7,110,804 B2 | 9/2006 | Baumer et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,246,069 B1 | 7/2007 | O'Hanlon et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,270,126 B2 | 9/2007 | Wallace et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,361,148 B2 | 4/2008 | Narimatsu |
| 7,368,855 B2 | 5/2008 | Orten |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,469,158 B2 | 12/2008 | Cutler et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |

(56) References Cited

U.S. PATENT DOCUMENTS

| | | |
|---|---|---|
| 7,509,494 B2 | 3/2009 | Al-Ali |
| 7,510,849 B2 | 3/2009 | Schurman et al. |
| 7,515,044 B2 | 4/2009 | Welch et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,625,117 B2 | 12/2009 | Haslett et al. |
| 7,647,083 B2 | 1/2010 | Al-Ali et al. |
| D609,193 S | 2/2010 | Al-Ali et al. |
| 7,662,105 B2 | 2/2010 | Hatlestad |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,783,056 B2 | 8/2010 | Wilmink |
| 7,791,155 B2 | 9/2010 | Diab |
| 7,801,581 B2 | 9/2010 | Diab |
| 7,806,226 B2 | 10/2010 | Drummond et al. |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,860,553 B2 | 12/2010 | Govari et al. |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,940,937 B2 | 5/2011 | Smith |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,976,480 B2 | 7/2011 | Grajales et al. |
| 7,988,637 B2 | 8/2011 | Diab |
| 7,988,688 B2 | 8/2011 | Webb et al. |
| 7,990,382 B2 | 8/2011 | Kiani |
| 7,991,165 B2 | 8/2011 | Kassal et al. |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,092,396 B2 | 1/2012 | Bagha et al. |
| 8,108,039 B2 | 1/2012 | Saliga et al. |
| RE43,169 E | 2/2012 | Parker |
| 8,118,620 B2 | 2/2012 | Al-Ali et al. |
| 8,121,673 B2 | 2/2012 | Tran |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali et al. |
| 8,229,533 B2 | 7/2012 | Diab et al. |
| 8,233,955 B2 | 7/2012 | Al-Ali et al. |
| 8,241,223 B2 | 8/2012 | Gavriely et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,291 B2 | 9/2012 | Bridger et al. |
| 8,265,723 B1 | 9/2012 | McHale et al. |
| 8,274,360 B2 | 9/2012 | Sampath et al. |
| 8,275,140 B2 | 9/2012 | Smith |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| 8,320,576 B1 | 11/2012 | Abbruscato |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,396,228 B2 | 3/2013 | Bilan |
| 8,399,822 B2 | 3/2013 | Al-Ali |
| 8,401,602 B2 | 3/2013 | Kiani |
| 8,403,865 B2 | 3/2013 | Halperin et al. |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,449,469 B2 | 5/2013 | Banet et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,491,489 B2 | 7/2013 | Shin et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,517,981 B2 | 8/2013 | Zornow |
| 8,523,781 B2 | 9/2013 | Al-Ali |
| 8,526,665 B2 | 9/2013 | Lutz et al. |

(56) References Cited

U.S. PATENT DOCUMENTS

| | | |
|---|---|---|
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,595 B2 | 2/2014 | Basinger |
| 8,641,631 B2 | 2/2014 | Sierra et al. |
| 8,652,060 B2 | 2/2014 | Al-Ali et al. |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,189 B2 | 4/2014 | Shennib |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali et al. |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,961,413 B2 | 2/2015 | Teller et al. |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,351 B1 | 11/2015 | Telfort et al. |
| 9,326,712 B1 | 5/2016 | Kiani |
| 9,370,335 B2 | 6/2016 | Al-Ali et al. |
| 9,386,961 B2 | 7/2016 | Al-Ali et al. |
| 9,538,980 B2 | 1/2017 | Telfort et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 2003/0149349 A1 | 8/2003 | Jensen |
| 2003/0196660 A1 | 10/2003 | Haveri |
| 2004/0215094 A1 | 10/2004 | Baumer et al. |
| 2005/0033128 A1 | 2/2005 | Ali |
| 2005/0065417 A1 | 3/2005 | Ali |
| 2006/0047215 A1 | 3/2006 | Newman et al. |
| 2006/0094943 A1 | 5/2006 | Van Slyke |
| 2006/0184052 A1 | 8/2006 | Iwasawa |
| 2006/0190051 A1 | 8/2006 | Gerber et al. |
| 2006/0198533 A1 | 9/2006 | Wang |
| 2006/0264767 A1 | 11/2006 | Shennib |
| 2007/0016030 A1 | 1/2007 | Stringer |
| 2007/0049837 A1 | 3/2007 | Shertukde et al. |
| 2007/0058818 A1 | 3/2007 | Yoshimine |
| 2007/0106179 A1 | 5/2007 | Bagha et al. |
| 2007/0147639 A1 | 6/2007 | Richardson et al. |
| 2007/0165872 A1 | 7/2007 | Bridger et al. |
| 2007/0167855 A1 | 7/2007 | Shin et al. |
| 2007/0173730 A1 | 7/2007 | Bikko |
| 2007/0208262 A1 | 9/2007 | Kovacs |
| 2007/0255153 A1 | 11/2007 | Kumar et al. |
| 2007/0282174 A1 | 12/2007 | Sabatino |
| 2008/0039735 A1 | 2/2008 | Hickerson |
| 2008/0076972 A1 | 3/2008 | Dorogusker et al. |
| 2008/0077026 A1 | 3/2008 | Banet et al. |
| 2008/0077435 A1 | 3/2008 | Muradia |
| 2008/0093157 A1 | 4/2008 | Drummond et al. |
| 2008/0097249 A1 | 4/2008 | Pool et al. |
| 2008/0139953 A1 | 6/2008 | Baker et al. |
| 2008/0188733 A1 | 8/2008 | Al-Ali et al. |
| 2008/0188760 A1 | 8/2008 | Al-Ali |

(56) References Cited

U.S. PATENT DOCUMENTS

| | | |
|---|---|---|
| 2008/0219464 A1 | 9/2008 | Smith |
| 2008/0251313 A1 | 10/2008 | Knight et al. |
| 2009/0076363 A1 | 3/2009 | Bly et al. |
| 2009/0093687 A1 | 4/2009 | Telfort et al. |
| 2009/0170664 A1 | 7/2009 | Shirasaki |
| 2009/0247924 A1 | 10/2009 | Lamego et al. |
| 2009/0275844 A1 | 11/2009 | Al-Ali |
| 2009/0299157 A1 | 12/2009 | Telfort et al. |
| 2009/0316925 A1 | 12/2009 | Eisenfeld et al. |
| 2010/0004518 A1 | 1/2010 | Vo et al. |
| 2010/0030040 A1 | 2/2010 | Poeze et al. |
| 2010/0069725 A1 | 3/2010 | Al-Ali |
| 2010/0090901 A1 | 4/2010 | Smith et al. |
| 2010/0094096 A1 | 4/2010 | Petruzzelli et al. |
| 2010/0204996 A1 | 8/2010 | Zeng et al. |
| 2010/0261979 A1 | 10/2010 | Kiani |
| 2010/0305416 A1 | 12/2010 | Bédard et al. |
| 2010/0317936 A1 | 12/2010 | Al-Ali et al. |
| 2011/0001605 A1 | 1/2011 | Kiani et al. |
| 2011/0028802 A1 | 2/2011 | Addison et al. |
| 2011/0034831 A1 | 2/2011 | Christensen et al. |
| 2011/0082711 A1 | 4/2011 | Poeze et al. |
| 2011/0105854 A1 | 5/2011 | Kiani et al. |
| 2011/0125060 A1 | 5/2011 | Telfort et al. |
| 2011/0172561 A1 | 7/2011 | Kiani et al. |
| 2011/0172967 A1 | 7/2011 | Al-Ali et al. |
| 2011/0196211 A1 | 8/2011 | Al-Ali |
| 2011/0208015 A1 | 8/2011 | Welch et al. |
| 2011/0209915 A1 | 9/2011 | Fechter et al. |
| 2011/0213212 A1 | 9/2011 | Al-Ali |
| 2011/0213273 A1 | 9/2011 | Telfort et al. |
| 2011/0230733 A1 | 9/2011 | Al-Ali |
| 2011/0237911 A1 | 9/2011 | Lamego et al. |
| 2011/0288431 A1 | 11/2011 | Alshaer et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0230523 A1 | 9/2012 | Ehrlund |
| 2012/0232427 A1 | 9/2012 | Bakema et al. |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0302920 A1 | 11/2012 | Bridger et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0338461 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317327 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0324817 A1 | 12/2013 | Diab |
| 2013/0331670 A1 | 12/2013 | Kiani |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0303520 A1 | 10/2014 | Telfort et al. |
| 2014/0309506 A1 | 10/2014 | Lamego et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0025406 A1 | 1/2015 | Al-Ali |
| 2015/0099998 A1 | 4/2015 | Christensen et al. |
| 2016/0045118 A1 | 2/2016 | Kiani |
| 2016/0066879 A1 | 3/2016 | Telfort et al. |
| 2017/0007198 A1 | 1/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |

FOREIGN PATENT DOCUMENTS

| | | |
|---|---|---|
| CN | 201497610 | 6/2010 |
| CN | 202005761 | 10/2011 |

(56) References Cited

FOREIGN PATENT DOCUMENTS

| | | |
|---|---|---|
| EP | 0716628 | 12/1998 |
| EP | 0659058 | 1/1999 |
| EP | 0956820 | 11/1999 |
| EP | 1207536 | 5/2002 |
| EP | 1518442 | 3/2005 |
| EP | 2014234 | 1/2009 |
| EP | 2391273 | 12/2011 |
| EP | 2488106 | 8/2012 |
| EP | 2488978 | 8/2012 |
| EP | 2710959 | 3/2014 |
| FR | 2847796 | 6/2004 |
| GB | 2358546 | 7/2001 |
| JP | S56-031742 A | 3/1961 |
| JP | S53-094482 A | 8/1978 |
| JP | 60059900 | 4/1985 |
| JP | 6214898 | 1/1987 |
| JP | 01-309872 | 12/1989 |
| JP | H04-317637 A | 11/1992 |
| JP | H07-152553 A | 6/1995 |
| JP | 10-155755 | 6/1998 |
| JP | 2001-50713 | 2/2001 |
| JP | 2003-329719 | 11/2003 |
| JP | 2005-522292 A | 7/2005 |
| JP | 2005-531230 A | 10/2005 |
| JP | 2012-513872 | 6/2012 |
| JP | 2013-508029 | 3/2013 |
| JP | 2013-508030 | 3/2013 |
| NO | 20040819 | 4/2003 |
| WO | WO 1994/005207 | 3/1994 |
| WO | WO 1994/013207 | 6/1994 |
| WO | WO 1995/029632 | 11/1995 |
| WO | WO 1999/053277 | 10/1999 |
| WO | WO 2000/010462 | 3/2000 |
| WO | WO 2001/034033 | 5/2001 |
| WO | WO 2001/078059 | 10/2001 |
| WO | WO 2001/87005 | 11/2001 |
| WO | WO 2001/097691 | 12/2001 |
| WO | WO 2002/003042 | 1/2002 |
| WO | WO 2002/24067 | 3/2002 |
| WO | WO 2003/058646 | 7/2003 |
| WO | WO 2003/087737 | 10/2003 |
| WO | WO 2004/000111 | 12/2003 |
| WO | WO 2004/004411 | 1/2004 |
| WO | WO 2004078038 | 9/2004 |
| WO | WO 2005/096931 | 10/2005 |
| WO | WO 2005/099562 | 10/2005 |
| WO | WO 2008/017246 | 2/2008 |
| WO | WO 2008/148172 | 12/2008 |
| WO | WO 2009/137524 | 11/2009 |
| WO | WO 2009/155593 | 12/2009 |
| WO | WO 2010/078168 | 7/2010 |
| WO | WO 2011/047207 | 4/2011 |
| WO | WO 2011/047209 | 4/2011 |
| WO | WO 2011/047213 | 4/2011 |
| WO | WO 2011/047216 | 4/2011 |
| WO | WO 2011/0147211 | 4/2011 |
| WO | WO 2013/056141 | 4/2013 |

OTHER PUBLICATIONS

US 8,845,543, 09/2014, Diab et al. (withdrawn)
Oversampling by Wikipedia, the free encyclopedia, pub. Online Oct. 7, 2012 at "https://wikipedia.org/w/index.php?title=Oversampling&oldid=516454012", accessed Sep. 3, 2015 in 3 pages.
Pseudorandom noise by Wikipedia, the free encyclopedia, pub. Online Jul. 25, 2012 at "https://wikipedia.org/w/index.php?title=Pseudorandom_noise&oldid=504121479", accessed Sep. 3, 2015 in 2 pages.
Noise generator by Wikipedia, the free encyclopedia, pub. Online May 6, 2012 at "https://wikipedia.org/w/index.php?title=Noise_generator&oldid=490897729", accessed Sep. 3, 2015 in 3 pages.
EP Office Action dated Jul. 11, 2016 in application No. 10779086.7 in 5 pages.
Analog Devices, 12-Bit Serial Input Multiplying D/A Converter, Product Data Sheet, 2000.
Avago Technologies, "HCNR200 and HCNR201, High-Linearity Analog Optocouplers," Data Sheet, Avago Technologies dated Nov. 18, 2008 in 19 pages.
Eldor et al., "A device for monitoring ventilation during anaesthesia; the paratracheal audible respiratory monitor", Canadian Journal of Anaesthesia, 1990, vol. 9, No. 1, p. 95-98.
Images showing tear down of a Measurement Specialties' stethoscope, Images taken on Sep. 7, 2007 in 38 pages.
International Preliminary Report on Patentability (IPRP) in PCT/US2010/052754 dated Apr. 26, 2012 in 11 pages.
International Preliminary Report on Patentability in PCT/US2010/052763 dated Apr. 17, 2012 in 9 pages.
International Search Report & Written Opinion in PCT Application PCT/US2010/058981 dated Feb. 17, 2011 in 11 pages.
International Search Report and Written Opinion in PCT Application No. PCT/US2012/060084 dated Dec. 21, 2012 in 11 pages.
International Search Report and Written Opinion in PCT Application PCT/US2010/052758 dated Feb. 10, 2011 in 12 pages.
International Search Report and Written Opinion in PCT/US2009/042902 dated Aug. 12, 2009 in 19 pages.
International Search Report and Written Opinion in PCT/US2010/052754 dated Jul. 27, 2011 in 17 pages.
International Search Report and Written Opinion in PCT/US2010/052756 dated Feb. 6, 2012 in 15 pages.
International Search Report and Written Opinion in PCT/US2010/052760 dated Mar. 8, 2011 in 9 pages.
International Search Report and Written Opinion in PCT/US2010/052763, dated May 13, 2011.
International Search Report and Written Opinion issued in PCT Application No. PCT/US2009/069287 dated Jun. 30, 2010 in 21 pages.
International Search Report in PCT Application PCT/CA2003/000536 dated Dec. 11, 2003 in 2 pages.
International Search Report in PCT Application PCT/US2009/069287 dated Mar. 30, 2010 in 7 pages.
Japanese Office Action re Application No. 2007-506626, dated Mar. 1, 2011.
Office Action issued in European Application No. 03711767.8 dated May 18, 2011 in 6 pages.
Office Action issued in European Application No. 10779086.7 dated Mar. 5, 2013 in 5 pages.
PCT Invitation to Pay Fees and Initial Search Report in PCT/US2009/069287 dated Apr. 21, 2010 in 6 pages.
PCT Invitation to Pay Fees and Initial Search Report in PCT/US2010/052754 dated Mar. 15, 2011.
PCT Invitation to Pay Fees and Initial Search Report in PCT/US2010/052756 dated Oct. 5, 2011 in 4 pages.
Sierra, G., et al. "Monitoring Respiratory Rate Based on Tracheal Sounds. First Experiences", Proceedings of the 26th Annual International Conference of the IEEE EMBS, Sep. 2004, pp. 317-320.
WelchAllyn OEM Technologies, ECG ASIC, ECG 3-lead, 5-lead, 12-lead and RESP Signal Processing, ECG ASIC Part No. 000.91163 (2001) in 84 pages.
P. White, "Advanced Compression Techniques, Tips & Tricks", Part 1 and Part 2, Dec. 2000 and Jan. 2001 in 11 pages.
Office Action in Japanese Application No. 2011-544508 dated Apr. 30, 2014.
International Preliminary Report on Patentability dated Apr. 15, 2014 for PCT Application No. PCT/US2012/060084.
European Search Report for Application No. 13185148.7 dated Dec. 6, 2013.
Office Action for Application No. 13185148.7 dated Apr. 4, 2017.

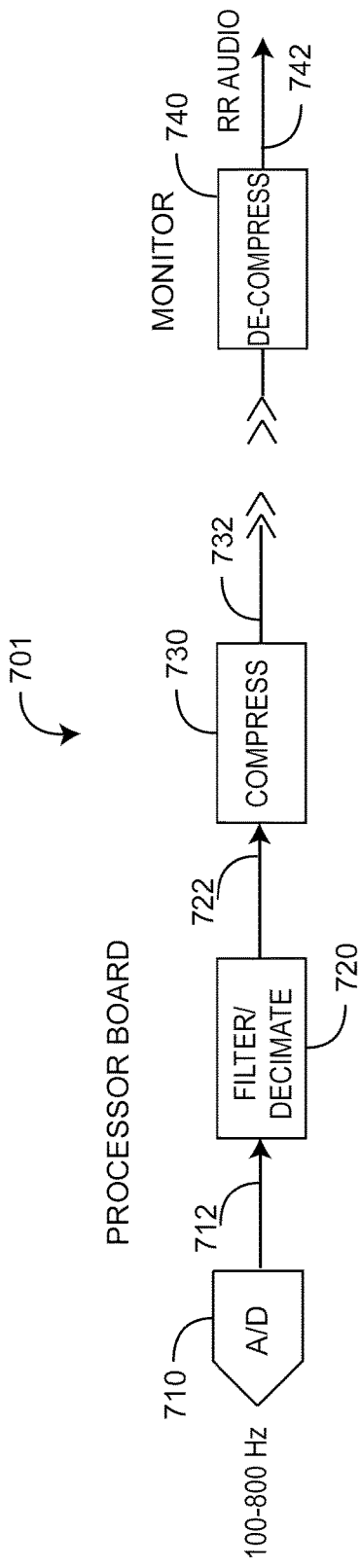
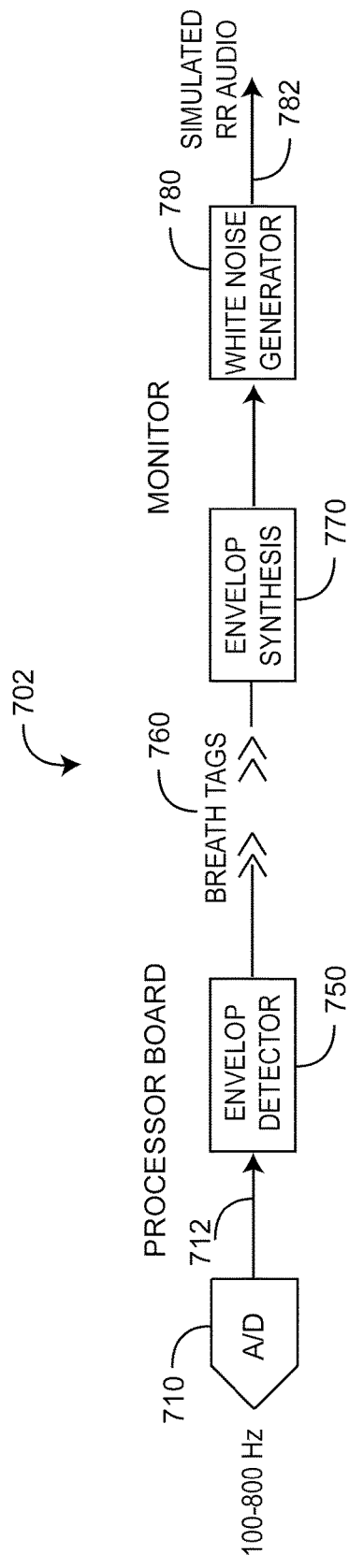
FIG. 7A
FIG. 7B

PHYSIOLOGICAL ACOUSTIC MONITORING SYSTEM

This application is a continuation of Ser. No. 14/473,831, filed Aug. 29, 2014, which is a divisional of U.S. patent application Ser. No. 12/905,036, filed Oct. 14, 2010, now U.S. Pat. No. 8,821,415, which claims the benefit of priority under 35 U.S.C. § 119(e) of U.S. Provisional Application No. 61/252,099, filed Oct. 15, 2009, and U.S. Provisional No. 61/391,098, filed Oct. 8, 2010, the disclosures of each of which are incorporated in their entirety by reference herein.

Additionally, this application relates to the following U.S. patent applications, the disclosures of which are incorporated in their entirety by reference herein:

| application Ser. No. | Filing Date | Title |
| --- | --- | --- |
| 60/893,853 | Mar. 8, 2007 | MULTI-PARAMETER PHYSIOLOGICAL MONITOR |
| 60/893,850 | Mar. 8, 2007 | BACKWARD COMPATIBLE PHYSIOLOGICAL SENSOR WITH INFORMATION ELEMENT |
| 60/893,858 | Mar. 8, 2007 | MULTI-PARAMETER SENSOR FOR PHYSIOLOGICAL MONITORING |
| 60/893,856 | Mar. 8, 2007 | PHYSIOLOGICAL MONITOR WITH FAST GAIN ADJUST DATA ACQUISITION |
| 12/044,883 | Mar. 8, 2008 | SYSTEMS AND METHODS FOR DETERMINING A PHYSIOLOGICAL CONDITION USING AN ACOUSTIC MONITOR |
| 61/252,083 | Oct. 15, 2009 | DISPLAYING PHYSIOLOGICAL INFORMATION |
| 12/904,836 | Oct. 14, 2010 | BIDIRECTIONAL PHYSIOLOGICAL INFORMATION DISPLAY |
| 12/904,823 | Oct. 14, 2010 | BIDIRECTIONAL PHYSIOLOGICAL INFORMATION DISPLAY |
| 61/141,584 | Dec. 30, 2008 | ACOUSTIC SENSOR ASSEMBLY |
| 61/252,076 | Oct. 15, 2009 | ACOUSTIC SENSOR ASSEMBLY |
| 12/643,939 | Dec. 21, 2009 | ACOUSTIC SENSOR ASSEMBLY |
| 61/313,645 | Mar. 12, 2010 | ACOUSTIC RESPIRATORY MONITORING SENSOR HAVING MULTIPLE SENSING ELEMENTS |
| 12/904,931 | Oct. 14, 2010 | ACOUSTIC RESPIRATORY MONITORING SENSOR HAVING MULTIPLE SENSING ELEMENTS |
| 12/904,890 | Oct. 14, 2010 | ACOUSTIC RESPIRATORY MONITORING SENSOR HAVING MULTIPLE SENSING ELEMENTS |
| 12/904,938 | Oct. 14, 2010 | ACOUSTIC RESPIRATORY MONITORING SENSOR HAVING MULTIPLE SENSING ELEMENTS |
| 12/904,907 | Oct. 14, 2010 | ACOUSTIC PATIENT SENSOR |
| 12/904,789 | Oct. 14, 2010 | ACOUSTIC RESPIRATORY MONITORING SYSTEMS AND METHODS |
| 61/252,062 | Oct. 15, 2009 | PULSE OXIMETRY SYSTEM WITH LOW NOISE CABLE HUB |
| 61/265,730 | Dec. 1, 2009 | PULSE OXIMETRY SYSTEM WITH ACOUSTIC SENSOR |
| 12/904,775 | Oct. 14, 2010 | PULSE OXIMETRY SYSTEM WITH LOW NOISE CABLE HUB |
| 61/331,087 | May 4, 2010 | ACOUSTIC RESPIRATION DISPLAY |

Many of the embodiments described herein are compatible with embodiments described in the above related applications. Moreover, some or all of the features described herein can be used or otherwise combined with many of the features described in the applications listed above.

BACKGROUND

The "piezoelectric effect" is the appearance of an electric potential and current across certain faces of a crystal when it is subjected to mechanical stresses. Due to their capacity to convert mechanical deformation into an electric voltage, piezoelectric crystals have been broadly used in devices such as transducers, strain gauges and microphones. However, before the crystals can be used in many of these applications they must be rendered into a form which suits the requirements of the application. In many applications, especially those involving the conversion of acoustic waves into a corresponding electric signal, piezoelectric membranes have been used.

Piezoelectric membranes are typically manufactured from polyvinylidene fluoride plastic film. The film is endowed with piezoelectric properties by stretching the plastic while it is placed under a high-poling voltage. By stretching the film, the film is polarized and the molecular structure of the plastic aligned. A thin layer of conductive metal (typically nickel-copper) is deposited on each side of the film to form electrode coatings to which connectors can be attached.

Piezoelectric membranes have a number of attributes that make them interesting for use in sound detection, including: a wide frequency range of between 0.001 Hz to 1 GHz; a low acoustical impedance close to water and human tissue; a high dielectric strength; a good mechanical strength; and piezoelectric membranes are moisture resistant and inert to many chemicals.

Due in large part to the above attributes, piezoelectric membranes are particularly suited for the capture of acoustic waves and the conversion thereof into electric signals and, accordingly, have found application in the detection of body sounds. However, there is still a need for a reliable acoustic sensor, particularly one suited for measuring bodily sounds in noisy environments.

SUMMARY

An aspect of an acoustic monitoring system has an acoustic front-end, a first signal path from the acoustic front-end directly to an audio transducer and a second signal path from the acoustic front-end to an acoustic data processor via an analog-to-digital converter. The acoustic front-end receives an acoustic sensor signal responsive to body sounds in a person. The audio transducer provides continuous audio of the body sounds. The acoustic data processor provides audio of the body sounds upon user demand.

In various embodiments, a second acoustic front-end receives a second acoustic sensor signal responsive to body sounds in a person. A third signal path is from the second acoustic front-end to a parameter processor via the analog-to-digital converter. The parameter processor derives a physiological measurement responsive to the body sounds. A fourth signal path is from the second acoustic front-end to the acoustic data processor via the analog-to-digital converter. The acoustic data processor provides a stereo audio output of the body sounds.

In other embodiments, the acoustic monitoring system further comprises a communications link to a remote site via a network. A trigger is responsive to the physiological measurement. A notification is transmitted over the communications link according to the trigger. The notification alerts an individual at the remote site of the physiological measurement and allows the individual to request the body sounds be downloaded to the individual via the communications link. An optical front-end receives an optical signal responsive to pulsatile blood flow at a tissue site on the person. The parameter processor derives a second physiological measurement responsive to the pulsatile blood flow.

The trigger is responsive to a combination of the physiological measurement and the second physiological measurement.

Further embodiments comprise acoustic filters implemented in the acoustic data processor. The filters define a series of audio bandwidths. Controls are in communications with the acoustic data processor. The controls are configured to adjust the audio bandwidths. The stereo audio output is adjusted by the controls so as to emphasize at least one of the audio bandwidths and deemphasize at least one other of the audio bandwidths so that a user of the controls can focus on a particular aspect of the stereo body sound output. The acoustic monitoring system further comprises a display that is responsive in real-time to the stereo audio output.

Another aspect of an acoustic monitoring system inputs a sensor signal responsive to body sounds of a living being. The sensor signal routes to an audio output device so as to enable a first user to listen to the body sounds. The sensor signal is digitized as acoustic data, and the acoustic data is transmitted to a remote device over a network. The acoustic data is reproduced on the remote device as audio so as to enable a second user to listen to the body sounds.

In various embodiments, the acoustic data is transmitted when a request is received from the remote device to transmit the body sounds. The request is generated in response to the second user actuating a button on the remote device to listen-on-demand. Further, a physiological event is detected in the sensor signal and a notification is sent to the second user in response to the detected event. The acoustic data transmission comprises an envelope extracted from the acoustic data and a breath tag sent to the remote device that is representative of the envelope.

In other embodiments, the reproduced acoustic data comprises the synthesized envelope at the remote device in response to the breath tag, where the envelope is filled with white noise. The reproduced acoustic data may also comprise the envelope modified with a physiological feature derived from the breath tag. The acoustic data may be stored on a mass storage device as a virtual tape. A searchable feature of the contents of the virtual tape in logged in a database and the virtual tape is retrieved from the mass storage device according to the searchable feature.

A further aspect of an acoustic monitoring system has an acoustic sensor, a sensor interface and a wireless communications device comprising a first monitor section. The acoustic sensor has a piezoelectric assembly, an attachment assembly and a sensor cable. The attachment assembly retains the piezoelectric assembly and one end of the sensor cable. The attachment assembly has an adhesive so as to removably attach the piezoelectric assembly to a tissue site. The other end of the sensor cable is communications with a sensor interface so as to activate the piezoelectric assembly to be responsive to body sounds transmitted via the tissue site. The wireless communications device is responsive to the sensor interface so as to transmit the body sounds remotely.

The acoustic monitor has a second wireless communications device and an audio output device comprising a second monitor section. The second wireless communications device is responsive to the wireless communications device so as to receive the body sounds. The audio output device is responsive to the second wireless communications device so as to audibly and continuously reproduce the body sounds.

The first monitor section is located near a living person and the second wireless communications device is located remote from the living person and attended to by a user. The sensor is adhesively attached to the living person so that the user hears the body sounds from the living person via the sensor and a continuous audio output. In an embodiment, the first monitor section is located proximate to an infant, the sensor is adhesively attached to the infant, the second monitor section is located remote to the infant proximate the adult and the continuous audio output allows the adult to monitor the infant so as to avoid sudden infant death syndrome (SIDS).

BRIEF DESCRIPTION OF THE DRAWINGS

FIG. 2A illustrates a neck sensor for physiological measurements and a chest sensor for monaural body sound monitoring;

FIG. 2B illustrates a dual acoustic sensor for stereo body sound monitoring;

FIGS. 7A-B are block diagrams illustrating an acoustic-envelope-based breath sound generator;

DETAILED DESCRIPTION OF THE PREFERRED EMBODIMENTS

Figure 1:
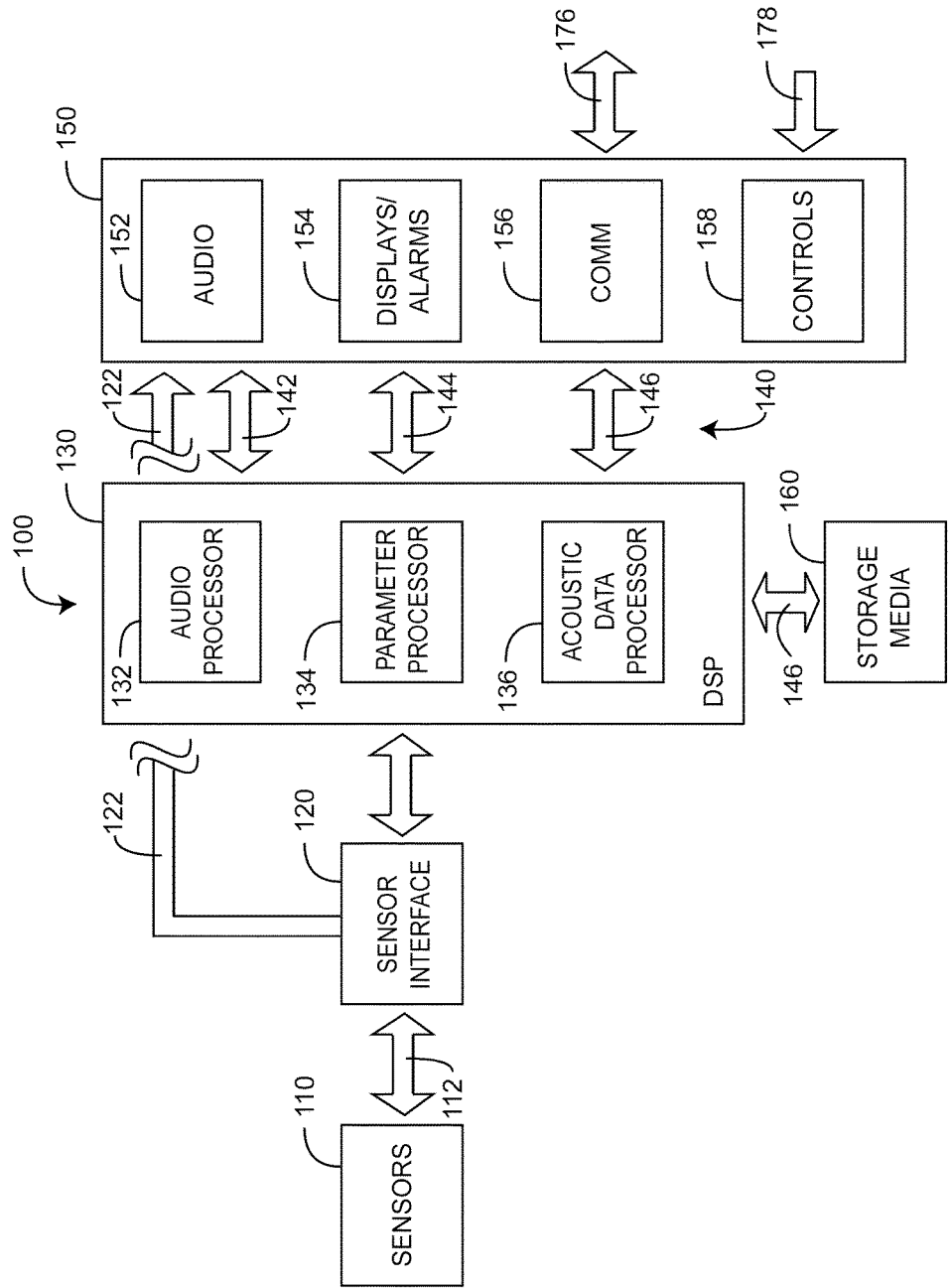
FIG. 1 is a general block diagram of a physiological acoustic monitoring system.

FIG. 1 generally illustrates a physiological acoustic monitoring system 100 embodiment having one or more sensors 110 in communications with one or more processors 130 via a sensor interface 120. The processors 130 both initiate and respond to input/output 150, including audio output 152, displays and alarms 154, communications 156 and controls 158. In an embodiment, the processors 130 are implemented in firmware executing on one or more digital signal processors (DSP), as described with respect to FIGS. 5-6, below. At least a portion of the sensors 110 generate acoustic signals, which may be directly utilized by the processors 130 or recorded onto or played back from storage media 160 or both.

The processors 130 include an audio processor 132 that outputs audio waveforms 142, a parameter processor 134 that derives physiological parameters 144 from sensor signals 112 and an acoustic data processor 136 that stores, retrieves and communicates acoustic data 146. Parameters include, as examples, respiration rate, heart rate and pulse rate. Audio waveforms include body sounds from the heart, lungs, gastrointestinal system and other organs. These body sounds may include tracheal air flow, heart beats and pulsatile blood flow, to name a few. Displays allow parameters 144 and acoustic data 146 to be visually presented to a user in various forms such as numbers, waveforms and graphs, as examples. Audio 152 allows audio waveforms to be reproduced through speakers, headphones or similar transducers. Raw audio 122 allows acoustic sensor signals 112 to be continuously reproduced through speakers, headphones or similar transducers, bypassing A/D conversion 120 and digital signal processing 130.

Storage media 160 allows acoustic data 146 to be recorded, organized, searched, retrieved and played back via the processors 130, communications 156 and audio output 152. Communications 156 transmit or receive acoustic data or audio waveforms via local area or wide area data networks or cellular networks 176. Controls 158 may cause the audio processor 132 to amplify, filter, shape or otherwise process audio waveforms 142 so as to emphasize, isolate, deemphasize or otherwise modify various features of an audio waveform or spectrum. In addition, controls 158 include buttons and switches 178, such as a "push to play" button that initiates local audio output 152 or remote transmission 176 of live or recorded acoustic waveforms.

As shown in FIG. 1, acoustic data 146 is initially derived from one or more acoustic sensor signals 112, along with, perhaps, other data inputs, such as from optical, blood pressure, EEG and ECG sensors, to name a few. The acoustic data 146 provides audio outputs 142, including audio respiration indicators, described with respect to FIGS. 8-9, below. The acoustic data 146, when analyzed, provides physiological parameters 144 that provide an indication of patient status, such as respiration rate or heart rate. Such analyses may result in visual or audible alerts or alarms 154 that are viewed locally or via notifications transmitted over local or wide area networks 176 to medical staff or other persons. Acoustic data 146 is utilized in real time or stored and retrieved for later use. Acoustic data 146 may be written on various storage media 160, such as a hard drive, and organized for convenient search and retrieval. In an embodiment, acoustic data 146 is advantageous organized on one or more hard drives as virtual magnetic tape so as to more easily manage, search, retrieve and playback acoustic data volumes. Further, the virtual tape volumes and/or the acoustic data itself may be entered into a database and organized as an acoustic library according to various search parameters including patient information, dates, corresponding physiological parameters and acoustic waveform features, to name a few. Applications for a physiological acoustic monitoring system include auscultation of body sounds by medical staff or by audio processors or both; SIDS monitoring; heart distress monitoring including the early detection and mitigation of myocardial infarction and cardiopulmonary arrest, as examples; and elder care, to name a few.

In an embodiment, sensor sounds 142 may be continuously "piped" to a remote device/listener or a central monitor or both. Listening devices may variously include pagers, cell phones, PDAs, electronic pads or tablets and laptops or other computers to name a few. Medical staff or other remote listeners are notified by the acoustic monitoring system according to flexible pre-programmed protocols to respond to the notification so as to hear breathing sounds, voice, heart sounds or other body sounds.

Figures 2A, 2B:
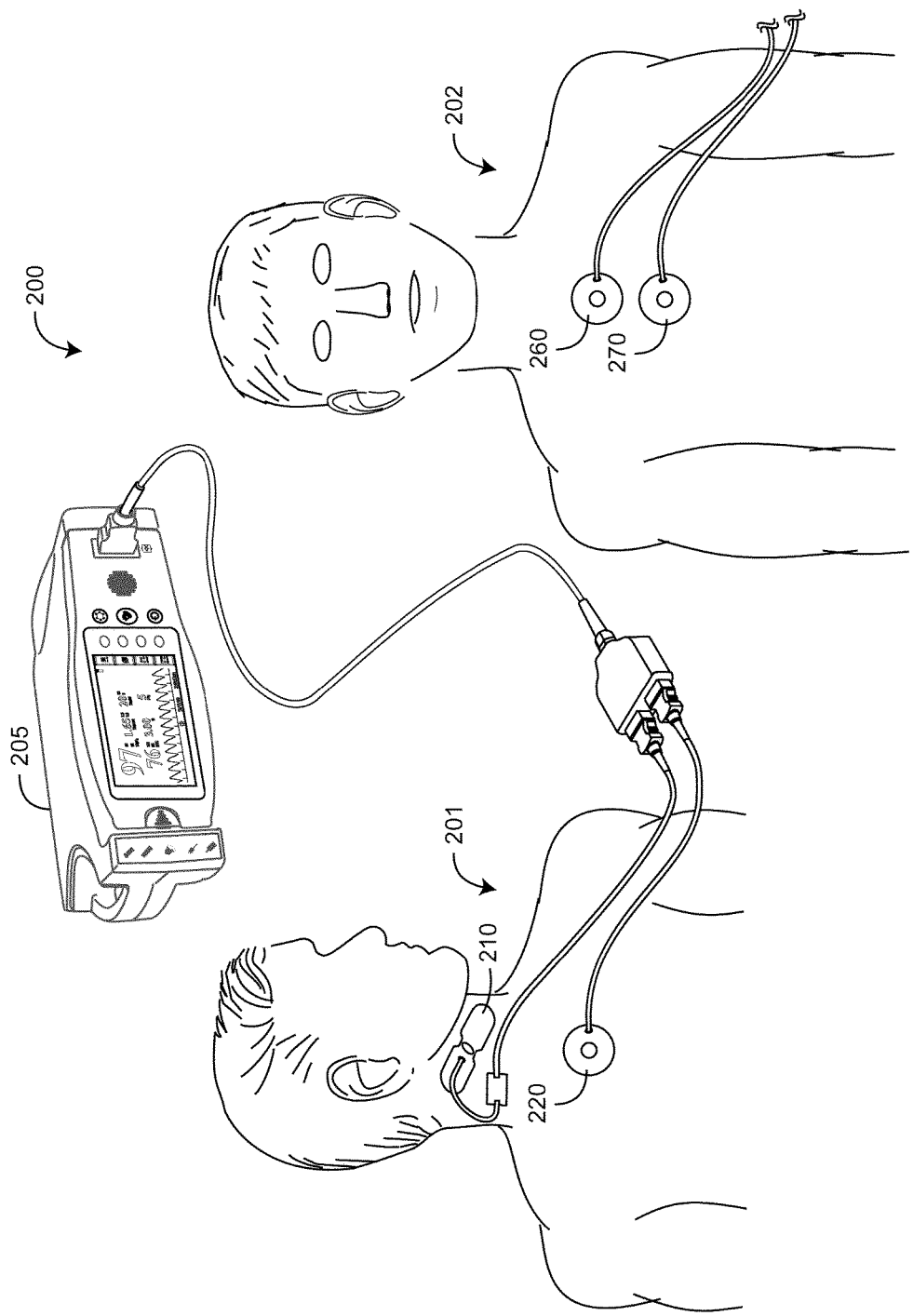
FIGS. 2A-B are illustrations of dual channel acoustic sensors.

FIGS. 2A-B illustrate physiological acoustic monitoring system 200 embodiments each having dual channel acoustic sensors 201, 202 in communications with a physiological monitor 205. As shown in FIG. 2A, a first acoustic sensor 210 is utilized for deriving one or more physiological parameters, such as respiration rate. A second acoustic sensor 220 is utilized to continuously monitor body sounds. In an embodiment, the second acoustic sensor 220 has a different color or shape than the first acoustic sensor 210 so as identify the sensor as a body sound listening device rather than an acoustic sensing device for determining a physiological parameter. In an embodiment, the body sound sensor 220 is placed over the heart to allow the monitoring of heart sounds or for determination of heart rate. In an embodiment, the body sound sensor 220 generates a signal that bypasses monitor digitization and signal processing so as to allow continuous listening of the unprocessed or "raw" body sounds. In particular, the first acoustic sensor 210 is neck-mounted so as to determine one or more physiological parameters, such as respiration rate. The second acoustic sensor 220 is chest-mounted for monaural heart sound monitoring. As shown in FIG. 2B, first and second acoustic sensors 260, 270 are mounted proximate the same body site but with sufficient spatial separation to allow for stereo sensor reception. In this manner, the listener can more easily distinguish and identify the source of body sounds.

Figure 3A:
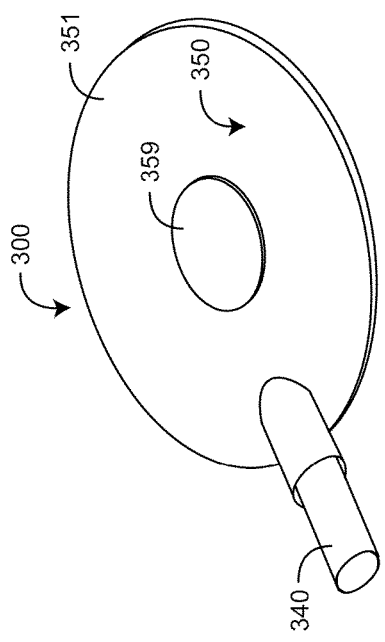
FIGS. 3A-B are top and bottom perspective views of a body sound sensor.
Figure 3B:
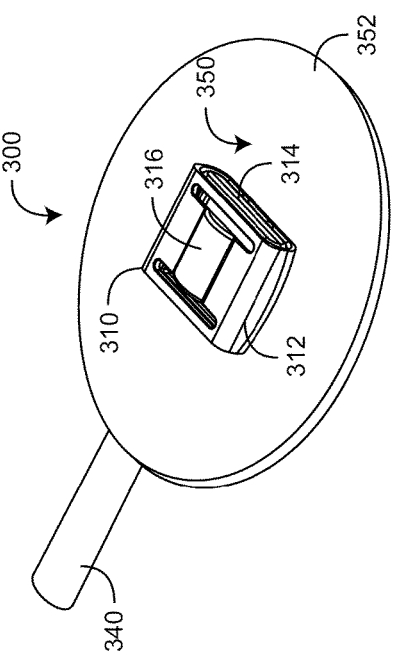

FIGS. 3A-B illustrate a body sound sensor 300 having acoustic 310, interconnect (not visible) and attachment 350 assemblies. The acoustic assembly 310 has an acoustic coupler 312 and a piezoelectric subassembly 314. The acoustic coupler 312 generally envelops or at least partially covers some or all of the piezoelectric subassembly 314. The piezoelectric subassembly 314 includes a piezoelectric membrane and a support frame (not visible). The piezoelectric membrane is configured to move on the frame in response to acoustic vibrations, thereby generating electrical signals indicative of body sounds. The acoustic coupler 312 advantageously improves the coupling between the acoustic signal measured at a skin site and the piezoelectric membrane. The acoustic coupler 312 includes a contact portion 316 placed against a person's skin.

Further shown in FIGS. 3A-B, the acoustic assembly 310 communicates with the sensor cable 340 via the interconnect assembly. In an embodiment, the interconnect assembly is a flex circuit having multiple conductors that are adhesively bonded to the attachment assembly 350. The interconnect assembly has a solder pad or other interconnect to interface with the sensor cable 340, and the attachment assembly 350 has a molded strain relief for the sensor cable. In an embodiment, the attachment assembly 350 is a generally circular, planar member having a top side 3511, a bottom side 352, and a center. A button 359 mechanically couples the acoustic assembly 310 to the attachment assembly center so that the acoustic assembly 310 extends from the bottom side 352. The sensor cable 340 extends from one end of the interconnect and attachment assemblies to a sensor connector at an opposite end so as to provide communications between the sensor and a monitor, as described in further detail with respect to, below. In an embodiment, an adhesive along the bottom side 352 secures the acoustic assembly 310 to a person's skin, such as at a neck, chest, back, abdomen site. A removable backing can be provided with the adhesive to protect the adhesive surface prior to affixing to a person's skin. In other embodiments, the attachment assembly 350 has a square, oval or oblong shape, so as to allow a uniform adhesion of the sensor to a measurement site. In a resposable embodiment, the attachment assembly 350 or portions thereof are removably detachable and attachable to the acoustic assembly 310 for disposal and replacement. The acoustic assembly 310 is reusable accordingly.

Figure 4:
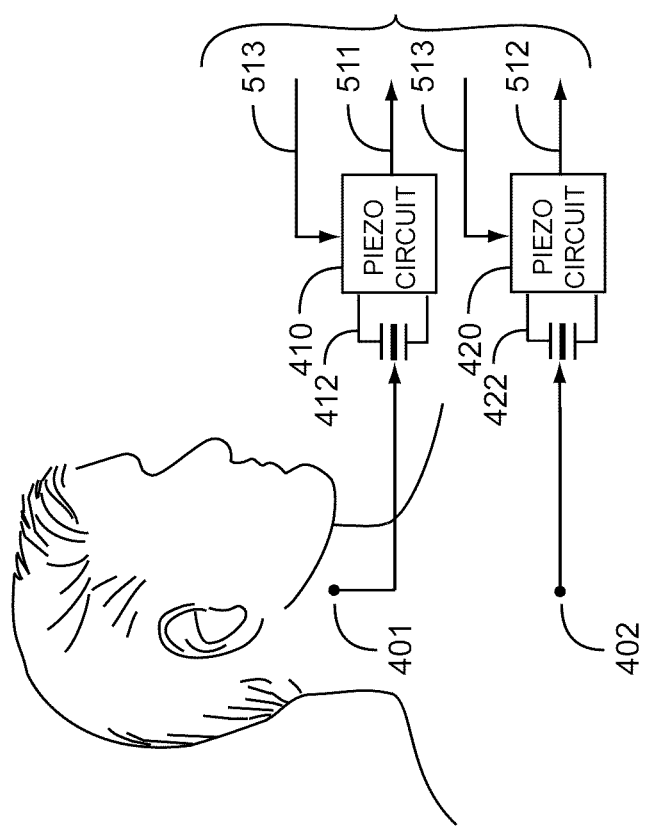
FIG. 4 is a general schematic diagram of acoustic and optic sensor drive elements.

FIG. 4 illustrates sensor elements for a multi-acoustic sensor configuration, including a power interface 513, piezo circuits 410, 420 and a piezoelectric membrane 412, 422 corresponding to each sensor head e.g. 210, 220 (FIG. 2A). The piezoelectric membrane senses vibrations and generates a voltage in response to the vibrations, as described with respect to the sensor of FIGS. 3A-B, above. The signal generated by the piezoelectric membrane is communicated to the piezo circuit 410, 420, described immediately below, and transmits the signal to the monitor 205 (FIG. 2A) for signal conditioning and processing. The piezo circuit 410 decouples the power supply 513 and performs preliminary signal conditioning. In an embodiment, the piezo circuit 410 includes clamping diodes to provide electrostatic discharge (ESD) protection and a mid-level voltage DC offset for the piezoelectric signal to ride on, to be superimposed on or to be added to. The piezo circuit 410 may also have a high pass filter to eliminate unwanted low frequencies such as below about 100 Hz for breath sound applications, and an op amp to provide gain to the piezoelectric signal. The piezo circuit 410 may also have a low pass filter on the output of the op amp to filter out unwanted high frequencies. In an embodiment, a high pass filter is also provided on the output in addition to or instead of the low pass filter. The piezo circuit may also provide impedance compensation to the piezoelectric membrane, such as a series/parallel combination used to control the signal level strength and frequency of interest that is input to the op amp. In one embodiment, the impedance compensation is used to minimize the variation of the piezoelectric element output. The impedance compensation can be constructed of any combination of resistive, capacitive and inductive elements, such as RC or RLC circuits.

Figure 5:
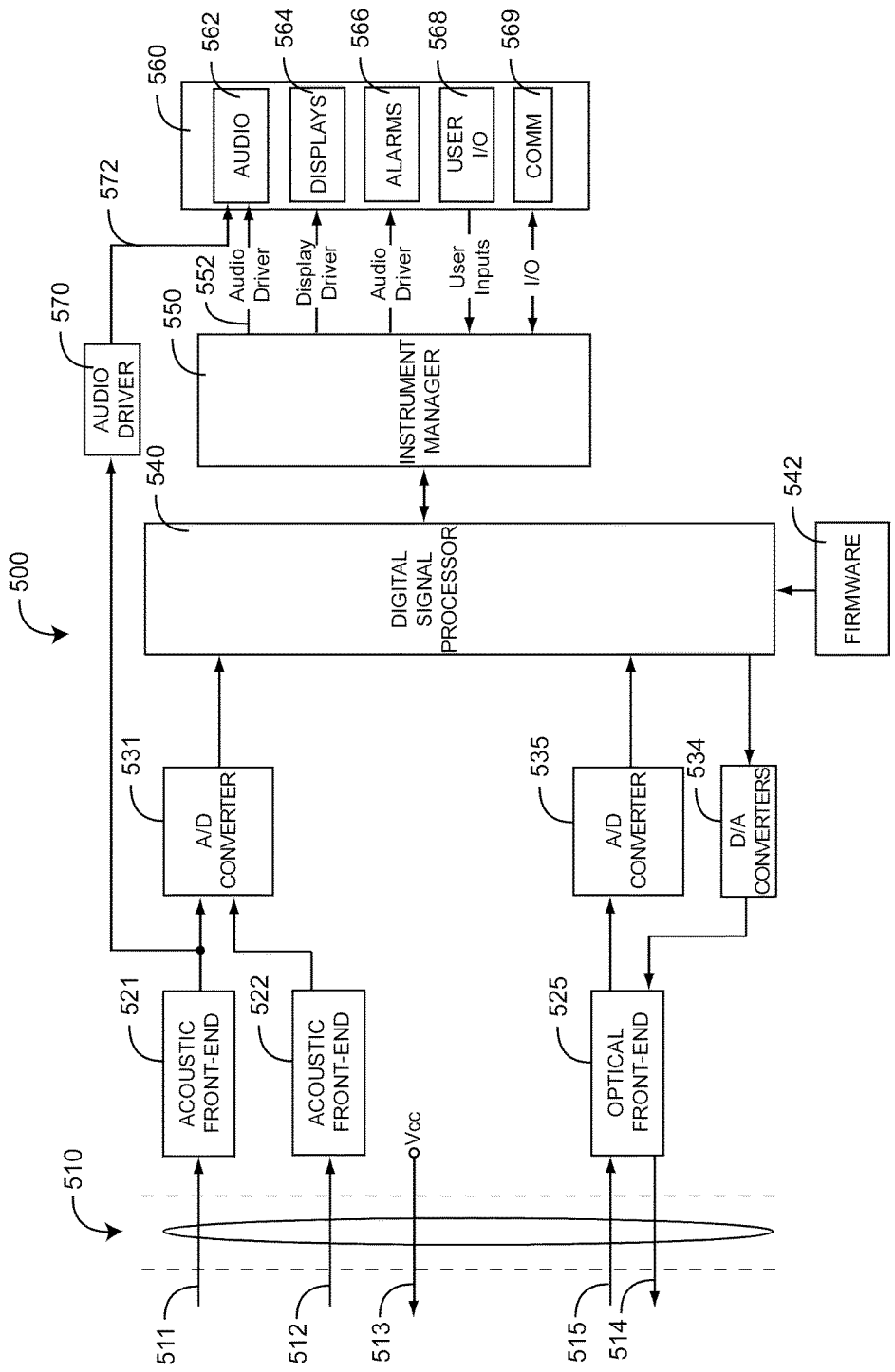
FIG. 5 is a general schematic diagram of a physiological acoustic monitor and corresponding sensor interface elements.

FIG. 5 illustrates a physiological acoustic monitor 500 for driving and processing signals from multi-acoustic sensor 401, 402 (FIG. 4). The monitor 500 includes one or more acoustic front-ends 521, 522, an analog-to-digital (A/D) converter 531, an audio driver 570 and a digital signal processor (DSP) 540. The DSP 540 can comprise a wide variety of data and/or signal processors capable of executing programs for determining physiological parameters from input data. In some embodiments, the monitor 500 also includes an optical front-end 525. In those embodiments, the monitor has an optical front-end 525, digital-to-analog (D/A) converters 534 and an A/D converter 535 to drive emitters and transform resulting composite analog intensity signal(s) from light sensitive detector(s) received via a sensor cable 510 into digital data input to the DSP 540. The acoustic front-ends 521, 522 and A/D converter 531 transform analog acoustic signals from a piezoelectric 410, 420 (FIG. 4) into digital data input to the DSP 540. The A/D converter 531 is shown as having a two-channel analog input and a multiplexed digital output to the DSP. In another embodiment, each front-end, communicates with a dedicated single channel A/D converter generating two independent digital outputs to the DSP. An acoustic front-end 521 can also feed an acoustic sensor signal 511 directly into an audio driver 570 for direct and continuous acoustic reproduction of the unprocessed sensor signal by a speaker, earphones or other audio transducer 562.

As shown in FIG. 5, the physiological acoustic monitor 500 may also have an instrument manager 550 that communicates between the DSP 540 and input/output 560. One or more I/O devices 560 have communications with the instrument manager 550 including displays, alarms, user I/O and instrument communication ports. Alarms 566 may be audible or visual indicators or both. The user I/O 568 may be, as examples, keypads, touch screens, pointing devices or voice recognition devices, to name a few. The displays 564 may be indicators, numerics or graphics for displaying one or more of various physiological parameters or acoustic data. The instrument manager 550 may also be capable of storing or displaying historical or trending data related to one or more of parameters or acoustic data.

As shown in FIG. 5, the physiological acoustic monitor 500 may also have a "push-to-talk" feature that provides a "listen on demand" capability. That is, a button 568 on the monitor is pushed or otherwise actuated so as to initiate acoustic sounds to be sent to a speaker, handheld device, or other listening device, either directly or via a network. The monitor 500 may also has a "mode selector" button or switch 568 that determines the acoustic content provided to a listener, either local or remote. These controls may be actuated local or at a distance by a remote listener. In an embodiment, push on demand audio occurs on an alarm condition in lieu of or in addition to an audio alarm. Controls 568 may include output filters like on a high quality stereo system so that a clinician or other user could selectively emphasize or deemphasize certain frequencies so as to hone-in on particular body sounds or characteristics.

In various embodiments, the monitor 500 may be one or more processor boards installed within and communicating with a host instrument. Generally, a processor board incorporates the front-end, drivers, converters and DSP. Accordingly, the processor board derives physiological parameters and communicates values for those parameters to the host instrument. Correspondingly, the host instrument incorporates the instrument manager and I/O devices. A processor board may also have one or more microcontrollers (not shown) for board management, including, for example, communications of calculated parameter data and the like to the host instrument.

Communications 569 may transmit or receive acoustic data or audio waveforms via local area or wide area data networks or cellular networks. Controls may cause the audio processor to amplify, filter, shape or otherwise process audio waveforms so as to emphasize, isolate, deemphasize or otherwise modify various features of the audio waveform or spectrum. In addition, switches, such as a "push to play" button can initiate audio output of live or recorded acoustic data. Controls may also initiate or direct communications.

Figure 6:
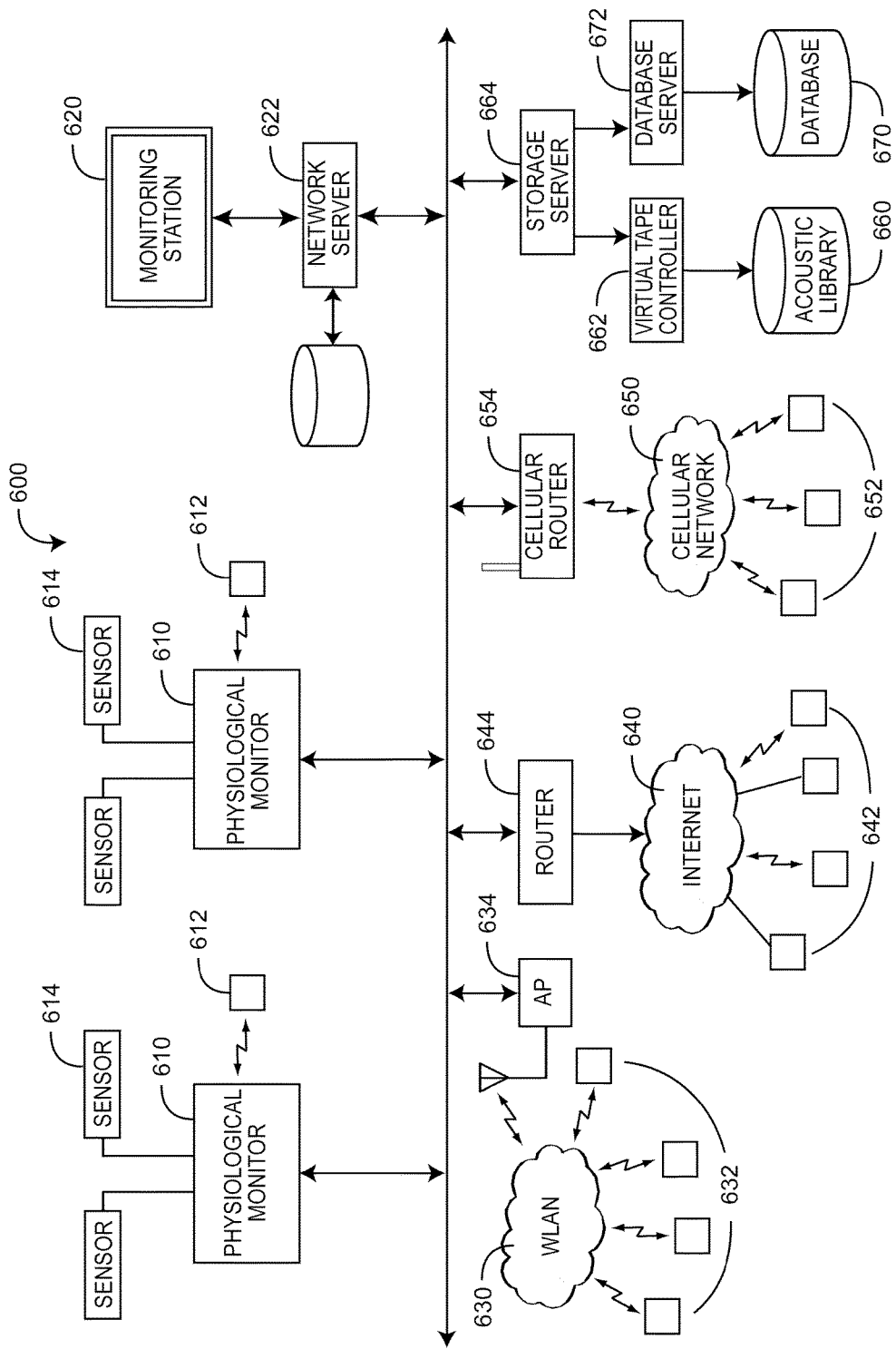
FIG. 6 is a network diagram for a physiological acoustic monitoring system.

FIG. 6 illustrates an acoustic physiological monitoring system 600 embodiment having a shared or open network architecture interconnecting one or more physiological monitors 610, monitoring stations 620 and mass storage 660. This interconnection includes proximity wireless devices 612 in direct wireless communication with a particular physiological monitor 610; local wireless devices 632 in communications with the monitors 610 via a wireless LAN 630; and distant wired or wireless devices 642, 652 in communications with the monitors 610 via WAN, such as Internet 640 or cellular networks 650. Communication devices may include local and remote monitoring stations 620 and wired or wireless communications and/or computing devices including cell phones, lap tops, pagers, PDAs, tablets and pads, to name a few. Physiological information is transmitted/received directly to/from end users over LAN or WAN. End users such as clinicians may carry wireless devices 632 in communications with the WLAN 630 so as to view in real-time physiological parameters or listen to audio data and waveforms on demand or in the event of an alarm or alert.

The network server 622 in certain embodiments provides logic and management tools to maintain connectivity between physiological monitors, clinician notification devices and external systems, such as EMRs. The network server 622 also provides a web based interface to allow installation (provisioning) of software related to the physiological monitoring system, adding new devices to the system, assigning notifiers to individual clinicians for alarm notification, escalation algorithms in cases where a primary caregiver does not respond to an alarm, interfaces to provide management reporting on alarm occurrences and internal journaling of system performance metrics such as overall system uptime. The network server 622 in certain embodiments also provides a platform for advanced rules engines and signal processing algorithms that provide early alerts in anticipation of a clinical alarm.

As shown in FIG. 6, audio data and corresponding audio files are advantageously stored on virtual tape 662, which provides the storage organization of tape cartridges without the slow, bulky, physical storage of magnetic tape and the corresponding human-operator intervention to physically locate and load physical cartridges into an actual tape-drive. A virtual tape controller 662 emulates standard tape cartridges and drives on modern, high capacity disk drive systems, as is well-known in the art. Accordingly, virtual "audio tapes" appear the same as physical tapes to applications, allowing the use of many existing cartridge tape storage, retrieval and archival applications. Further, while the upper-limit of a physical tape cartridge may be a few hundred megabytes, a virtual tape server 662 can be configured to provide considerably larger "tape" capacity. Mount-time is near-zero for a virtual tape and the data is available immediately. Also, while traditional physical tape systems have to read a tape from the beginning, moving sequentially through the files on the tape, a virtual drive can randomly access data at hard-disk speeds, providing tape I/O at disk access speeds.

Additionally shown in FIG. 6, a sound processing firmware module of certain embodiments accesses a database 670 of sound signatures 660 and compares the received signal with the entries in the database to characterize or identify sounds in the received signal. In another embodiment, the sound processing module generates and/or accesses a database 670 of sound signatures specific to a patient, or specific to a particular type of patient (e.g., male/female, pediatric/adult/geriatric, etc.). Samples from a person may be recorded and used to generate the sound signatures. In some embodiments, certain signal characteristics are used to identify particular sounds or classes of sounds. For example, in one embodiment, signal deviations of relatively high amplitude and or sharp slope may be identified by the sound processing module. Sounds identified in various embodiments by the sound processing module include, but are not limited to, breathing, speech, choking, swallowing, spasms such as larynx spasms, coughing, gasping, etc.

Once the sound processing module characterizes a particular type of sound, the acoustic monitoring system can, depending on the identified sound, use the characterization to generate an appropriate response. For example, the system may alert the appropriate medical personnel to modify treatment. In one embodiment, medical personnel may be alerted via an audio alarm, mobile phone call or text message, or other appropriate means. In one example scenario, the breathing of the patient can become stressed or the patient may begin to choke due to saliva, mucosal, or other build up around an endotracheal tube. In an embodiment, the sound processing module can identify the stressed breathing sounds indicative of such a situation and alert medical personnel to the situation so that a muscle relaxant medication can be given to alleviate the stressed breathing or choking.

According to some embodiments, acoustic sensors described herein can be used in a variety of other beneficial applications. For example, an auscultation firmware module may process a signal received by the acoustic sensor and provide an audio output indicative of internal body sounds of the patient, such as heart sounds, breathing sounds, gastrointestinal sounds, and the like. Medical personnel may listen to the audio output, such as by using a headset or speakers. In some embodiments the auscultation module allows medical personnel to remotely listen for patient diagnosis, communication, etc. For example, medical personnel may listen to the audio output in a different room in a hospital than the patient's room, in another building, etc. The audio output may be transmitted wirelessly (e.g., via Bluetooth, IEEE 802.11, over the Internet, etc.) in some embodiments such that medical personnel may listen to the audio output from generally any location.

FIGS. 7-8 illustrate alternative breath sound generators 701, 702 for providing an audio output for an acoustic sensor. As shown in FIG. 7A, acoustic sensor data is input to a processor board 701 so as to generate a corresponding breathing sound from a speaker or similar audio transducer. The audio data is A/D converted 710, down-sampled 720 and compressed 730. The monitor receives the compressed data 732, decompresses the data 740 and outputs the respiration audio 742 to a speaker. In an embodiment, the breath sound is combined with a pulse oximeter pulse "beep." However, unlike a pulse beep, this breath "beep" output may utilize nearly the full capacity of the processor board data channel 732.

Figure 8A:
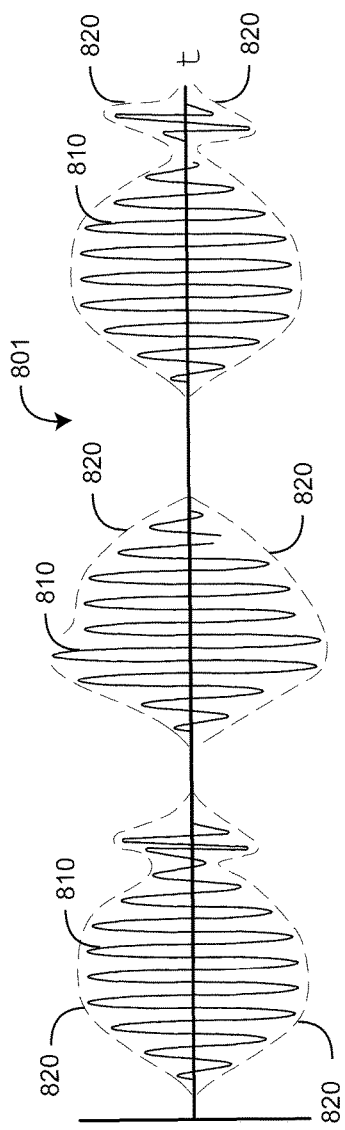
FIGS. 8A-C are graphs of illustrating an acoustic-envelope-based breath sound generator.
Figure 8B:
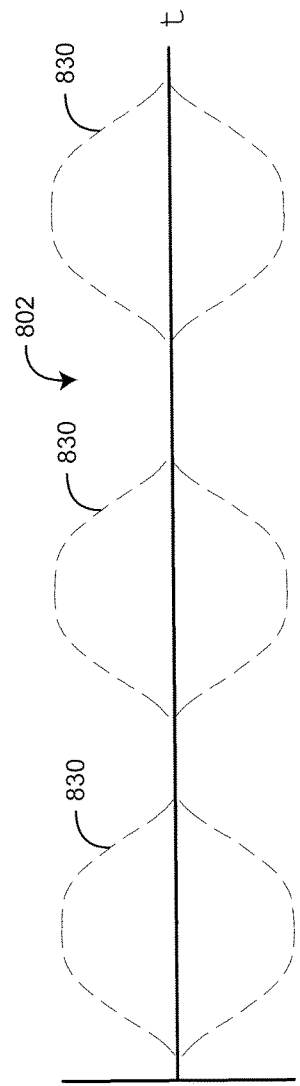
Figure 8C:
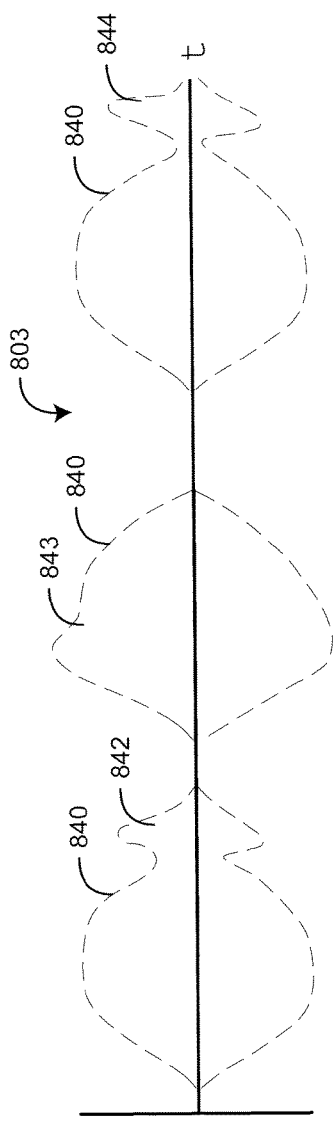

As shown in FIG. 7B and FIGS. 8A-C, an envelope-based breath sound generator advantageously provides breath sound reproduction at reduced data rates, which will not interfere with the data channel capacity of a signal processing board. Audio data is A/D converted 710 and input to an envelop detector 750. FIG. 8A illustrates a representative acoustic breath sound signal 810 derived by a neck sensor from tracheal air flow. The sound signal 810 has an envelope 820 with "pulses" corresponding to either inhalation or exhalation. The envelope detector 750 generates breath tags 760 describing the envelope 820. These breath tags 760 are transmitted to the monitor in lieu of the compressed audio signal described with respect to FIG. 7A, above. In one embodiment, the breath tags describe an idealized envelope 830, as shown in FIG. 8B. In another embodiment, the breath tags also include detected envelope features 842, 843, 844 that are characteristic of known acoustically-related phenomena such as wheezing or coughing, as examples. At the monitor end, envelop synthesis 770 reproduces the envelope 830 (FIG. 8B) and fills the envelope with an artificial waveform, such as white noise 780. This reconstructed or simulated breath signal is then output 782 to a speaker or similar device. In another embodiment, the breath tags are transmitted over a network to a remote device, which reconstructs the breathing waveform from the breath tags in like manner.

In various other embodiments, acoustic breathing waveforms are detected by an acoustic sensor, processed, transmitted and played on a local or remote speaker or other audio output from actual (raw) data, synthetic data and artificial data. Actual data may be compressed, but is a nearly complete or totally complete reproduction of the actual acoustic sounds at the sensor. Synthetic data may be a synthetic version of the breathing sound with the option of the remote listener to request additional resolution. Artificial data may simulate an acoustic sensor sound with minimal data rate or bandwidth, but is not as clinically useful as synthetic or actual data. Artificial data may, for example, be white noise bursts generated in sync with sensed respiration. Synthetic data is something between actual data and artificial data, such as the acoustic envelope process described above that incorporates some information from the actual sensor signal. In an embodiment breath sounds are artificially hi/lo frequency shifted or hi/lo volume amplified to distinguish inhalation/exhalation. In an embodiment, dual acoustic sensors placed along the neck are responsive to the relative time of arrival of tracheal sounds so as to distinguish inhalation and exhalation in order to appropriately generate the hi/lo frequency shifts.

Figure 9:
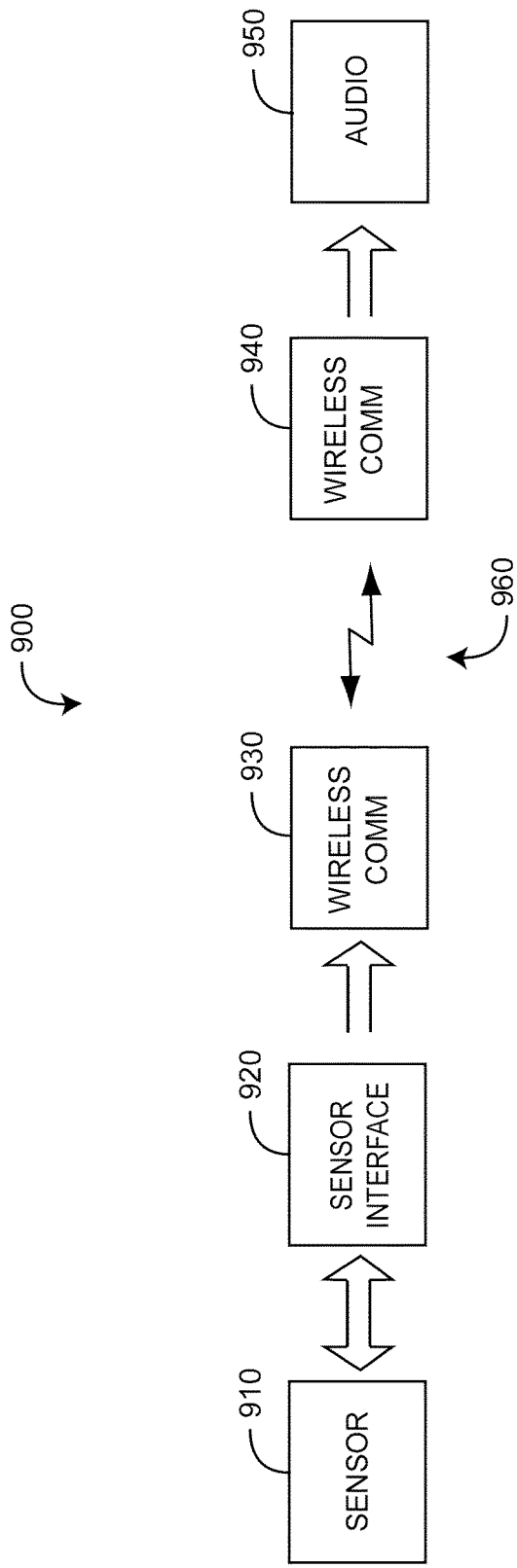
FIG. 9 is an illustration of a physiological acoustic monitoring system for out-patient monitoring applications.

FIG. 9 illustrates a physiological acoustic monitor 900 for out-patient applications, including sudden infant death syndrome (SIDS) prevention and elder care. The monitor 900 has a sensor section 901 and a remote section 902. The sensor section 901 has a sensor 910, a sensor interface 920 and a communications element 930. In an embodiment, the sensor 910 is an adhesive substrate integrated with a piezoelectric assembly and interconnect cable, such as described with respect to FIGS. 3A-B, above. The sensor interface 920 provides power to and receives the sensor signal from the sensor piezo circuit, as described with respect to FIGS. 4-5, above. The wireless communications element 930 receives the sensor signal from the sensor interface and transmits the signal to the corresponding communications element 940 in the remote section 902, which provides an amplified sensor signal sufficient to drive a small speaker. In an embodiment, the communications link 960 conforms with IEEE 802.15 (Bluetooth).

A physiological acoustic monitoring system has been disclosed in detail in connection with various embodiments. These embodiments are disclosed by way of examples only and are not to limit the scope of the claims that follow. One of ordinary skill in art will appreciate many variations and modifications.

What is claimed is:

1. A method of generating synthetic physiological sound responsive to a signal detected by an acoustic sensor attached to a patient, the method comprising:
processing, at a patient monitor, a signal from an acoustic sensor responsive to a piezoelectric modulation of the acoustic sensor;
detecting envelope features in the processed signal responsive to a periodic physiological process;
generating an idealized envelope based on the detected envelope features;
comparing the signal with sound signatures corresponding to physiological sounds stored in a first data repository;
detecting a physiological event from the processed signal based on the comparison of the signal with the sound signatures; and
generating a synthetic physiological sound comprising a first sound corresponding to the generated idealized envelope and a second sound corresponding to a portion of the processed signal with the detected physiological event.

2. The method of claim 1, wherein the physiological sounds comprise breathing, speech, chocking, swallow, spasms, coughing, gasping, heart, and gastrointestinal sounds.

3. The method of claim 1, wherein the idealized envelope is represented as breath tag.

4. The method of claim 3, further comprising transmitting the breath tag over a network in lieu of the processed signal.

5. The method of claim 4, further comprising transmitting the portion of the signal over the network.

6. The method of claim 5, further comprising compressing the portion of the signal prior to the transmission over the network.

7. The method of claim 1, wherein the synthetic physiological sound is generated on a first computing system remote from the physiological monitor.

8. A system for generating synthetic physiological sound responsive to a signal detected by an acoustic sensor attached to a patient, the system comprising one or more hardware processors configured to:
process a signal from an acoustic sensor responsive to a piezoelectric modulation of the acoustic sensor;
detect envelope features in the processed signal responsive to a periodic physiological process;
generate an idealized envelope based on the detected envelope features;
compare the signal with sound signatures corresponding to physiological sounds stored in a first data repository;
detect a physiological event from the processed signal based on the comparison of the signal with the sound signatures; and
generate a synthetic physiological sound comprising a first sound corresponding to the generated idealized envelope and a second sound corresponding to a portion of the processed signal with the detected physiological event.

9. The system of claim 8, wherein the physiological sounds comprise breathing, speech, chocking, swallow, spasms, coughing, gasping, heart, and gastrointestinal sounds.

10. The system of claim 8, wherein the idealized envelope is represented as breath tag.

11. The system of claim 10, wherein the one or more hardware processors are further configured to transmit the breath tag over a network in lieu of the processed signal.

12. The system of claim 11, wherein the one or more hardware processors are configured to transmit the portion of the signal over the network.

13. The system of claim 12, wherein the one or more hardware processors are further configured to compress the portion of the signal prior to the transmission over the network.

14. The system of claim 8, wherein the one or more hardware processors comprise a first hardware processor and second hardware processor located remotely from the first hardware processor over a network.

15. The system of claim 14, wherein the execution of the generation of the synthetic sound is executed by the second hardware processor.

16. A system for generating synthetic physiological sound responsive to a signal detected by an acoustic sensor attached to a patient, the system comprising:
means for processing signal from an acoustic sensor responsive to a piezoelectric modulation of the acoustic sensor;
means for detecting an envelope from the processed signal;
means for detecting a physiological event from the processed signal; and
means for generating a synthetic physiological sound based on the envelope detection and detected physiological event.

* * * * *